(12) United States Patent
Poel

(10) Patent No.: US 7,012,088 B2
(45) Date of Patent: Mar. 14, 2006

(54) INDOLONE OXAZOLIDINONES AND DERIVATIVES THEREOF

(75) Inventor: Toni-Jo Poel, Pinckney, MI (US)

(73) Assignee: Pharmacia & Upjohn Company, Kalamazoo, MI (US)

(*) Notice: Subject to any disclaimer, the term of this patent is extended or adjusted under 35 U.S.C. 154(b) by 109 days.

(21) Appl. No.: 10/762,838

(22) Filed: Jan. 22, 2004

(65) Prior Publication Data

US 2004/0176610 A1 Sep. 9, 2004

Related U.S. Application Data

(60) Provisional application No. 60/449,734, filed on Feb. 24, 2003.

(51) Int. Cl.
*A61K 31/422* (2006.01)
*C07D 263/28* (2006.01)

(52) U.S. Cl. .................. 514/376; 548/243; 548/466
(58) Field of Classification Search ............... 548/243, 548/466; 514/376
See application file for complete search history.

(56) References Cited

U.S. PATENT DOCUMENTS

| | | | |
|---|---|---|---|
| 5,164,510 A | 11/1992 | Brickner et al. | 548/231 |
| 5,225,565 A | 7/1993 | Brickner et al. | 548/229 |
| 5,529,998 A | 6/1996 | Habich et al. | 514/233.8 |
| 5,792,765 A | 8/1998 | Riedl et al. | 514/236.8 |
| 5,869,659 A | 2/1999 | Stolle et al. | 544/114 |
| 6,069,160 A | 5/2000 | Stolle et al. | 514/367 |

FOREIGN PATENT DOCUMENTS

| | | |
|---|---|---|
| EP | 0738726 B1 | 4/1996 |
| EP | 0738726 A1 | 4/1996 |
| WO | WO90/02744 | 3/1990 |
| WO | WO 95/07271 | 8/1994 |
| WO | WO 00/21960 | 10/1998 |
| WO | WO 00/29409 | 11/1998 |
| WO | WO 99/40094 | 1/1999 |
| WO | WO 99/64416 | 6/1999 |
| WO | WO 99/64417 | 6/1999 |
| WO | WO 01/47919 A1 | 12/2000 |
| WO | WO 01/81350 A1 | 4/2001 |
| WO | WO01/74812 A1 | 10/2001 |
| WO | WO02/102785 A1 | 12/2002 |
| WO | WO03/035073 A1 | 5/2003 |
| WO | WO03/072253 A | 9/2003 |

OTHER PUBLICATIONS

Bioorganic and Medicinal Chemistry Letters, Dec. 1, 2003, vol. 13, No. 23, pp. 4235–4239(5).*
Tetrahedron .Letter 1996, 37(44), 7937–7940.

* cited by examiner

*Primary Examiner*—Joseph K. McKane
*Assistant Examiner*—Janet L. Coppins
(74) *Attorney, Agent, or Firm*—Lucy X. Yang; Charles Ashbrook

(57) ABSTRACT

The present invention provides antibacterial agents of formula I described herein and intermediates for their preparation.

10 Claims, No Drawings

INDOLONE OXAZOLIDINONES AND DERIVATIVES THEREOF

CROSS REFERENCE TO RELATED APPLICATIONS

This application claims the benefit of the following provisional application: Application Ser. No. 60/449,734 filed Feb. 24, 2003 under 35 U.S.C. 119(e)(1).

FIELD OF THE INVENTION

The present invention relates to novel 2-oxindolyl (or indol-2-one)oxazolidinones, derivatives thereof, intermediates and their preparations.

BACKGROUND OF THE INVENTION

The oxazolidinone antibacterial agents are a novel synthetic class of antimicrobials with potent activity against a number of human and veterinary pathogens, including gram-positive aerobic bacteria such as multiply-resistant staphylococci and streptococci, anaerobic organisms such as bacteroides and clostridia species, and acid-fast organisms such as *Mycobacterium tuberculosis* and *Mycobacterium avium*.

SUMMARY OF THE INVENTION

In one aspect, the invention features compounds of Formula I

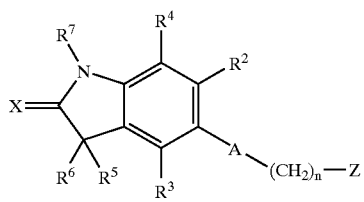

Formula I or a pharmaceutically acceptable salt thereof wherein:
A is structure i, ii, iii, or iv;

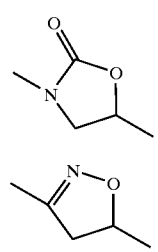  i

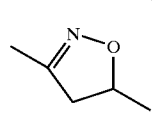  ii

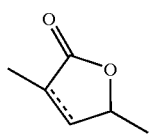  iii

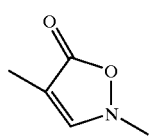  iv wherein the dashed line in formula iii represents an optional double bond;

n is 0 or 1;

X is O, S, NH, Nalkyl, NOH, and NOalkyl;

Z is $NHC(=O)R^1$, $NHC(=S)R^1$, $C(=O)NHR^1$, $C(=O)N(H)OH$, $NHC(=NCN)R^1$, $NH$-$het^1$, $O$-$het^1$, $S$-$het^1$, or $het^2$;

$R^1$ is H, $NH_2$, $NHC_{1-4}$allyl, $C_{1-4}$allyl, $C_{2-4}$alkenyl, $-(CH_2)_mC(=O)C_{1-4}$alkyl, $OC_{1-4}$alkyl, $SC_{1-4}$alkyl, $(CH_2)_mC_{3-6}$cycloalkyl, $CH=CH$-aryl, $CH=CH$-$het^1$, $CH_2C(=O)$-aryl, or $CH_2C(=O)$-$het^1$, the alkyl, aryl or het optionally being a substituted alkyl, substituted aryl or substituted het, respectively;

$R^2$ and $R^3$ are independently H or F;

$R^4$ is H, Cl, F, $CH_3$, $CF_3$, $NH_2$, $NO_2$ or CN;

$R^5$ and $R^6$ are independently H, alkyl, substituted alkyl, —Salkyl, —Oalkyl, alkenyl, substituted alkenyl, hydroxy, aryl, or halo;

$R^7$ is H, alkyl, substituted alkyl, cycloalkyl, $C(=O)$alkyl, $C(=O)$substituted alkyl, aryl, alkenyl, substituted alkenyl, het, substituted het, or substituted aryl;

$het^1$ is a C-linked five-(5) or six-(6) membered heterocyclic ring which contains 1–4 heteroatoms selected from oxygen, sulfur, and nitrogen;

$het^2$ is a N- or C-linked five-(5) or six-(6) membered heterocyclic ring which contains 1–4 heteroatoms selected from oxygen, sulfur, and nitrogen;

each m is independently 0, 1 or 2.

In another aspect, the invention features a compound of Formula II

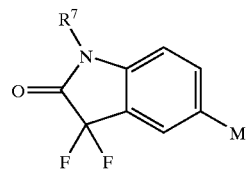

II wherein:
$R^7$ is alkyl of 1 to 4 carbons;
M is selected from the group consisting of $NO_2$, $NH_2$, $NHC(O)OR^8$, or structure i

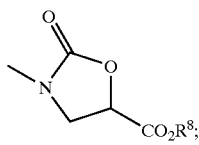

i wherein $R^8$ is alkyl of 1 to 4 carbons or benzyl.

In still another aspect, the invention features the use of a compound of formula I for preparing a medicament for treating microbial infections in mammals. The medicament is prepared for administration orally, parenterally, transdermally, or topically. The medicament may include a compound of formula I in an amount from about 0.1 to about 100 mg/kg of body weight/day, more preferably in an amount of from about 1 to about 50 mg/kg of body weight/day. For instance the medicament may include between about 0.1 and about 1000 mg, e.g., about 0.1 to about 500 mg, of a compound of formula I.

In yet another aspect, the invention features a pharmaceutical composition comprising a compound of formula I and a pharmaceutically acceptable carrier.

Advantageously, the compounds of this invention exhibit potent antibacterial activity.

DETAILED DESCRIPTION OF THE INVENTION

The following definitions are used, unless otherwise described.

The carbon atom content of various hydrocarbon-containing moieties is indicated by a prefix designating the minimum and maximum number of carbon atoms in the moiety, i.e., the prefix $C_{i-j}$ indicates a moiety of the integer "i" to the integer "j" carbon atoms, inclusive. Thus, for example, $C_{1-7}$ alkyl refers to alkyl of one to seven carbon atoms, inclusive.

The term "halo" refers to a halogen atom selected from Cl, Br, I, and F.

The term "alkyl" refers to both straight- and branched-chain moieties. Unless otherwise specifically stated, alkyl moieties include between 1 and 6 carbon atoms.

The term "alkenyl" refers to both straight- and branched-chain moieties containing at least one —C=C—. Unless otherwise specifically stated, alkenyl moieties include between 1 and 6 carbon atoms.

The term "alkynyl" refers to both straight- and branched-chain moieties containing at least one —C≡C—. Unless otherwise specifically stated, alkynyl moieties include between 1 and 6 carbon atoms.

The term "alkoxy" refers to —O-alkyl groups.

The term "cycloalkyl" refers to a cyclic alkyl moiety. Unless otherwise specifically stated cycloalkyl moieties will include between 3 and 7 carbon atoms.

The term "cycloalkenyl" refers to a cyclic alkenyl moiety. Unless otherwise specifically stated cycloalkenyl moieties will include between 3 and 7 carbon atoms and at least one —C=C— group within the cyclic ring.

The term "amino" refers to —NH$_2$.

The term "aryl" refers to phenyl and naphthyl.

The term "het" refers to mono- or bicyclic ring systems containing at least one heteroatom selected from O, S, and N. Each monocyclic ring may be aromatic, saturated, or partially unsaturated. A bicyclic ring system may include a monocyclic ring containing at least one heteroatom fused with a cycloalkyl or aryl group. A bicyclic ring system may also include a monocyclic ring containing at least one heteroatom fused with another het, monocyclic ring system. The term het encompasses the terms het$^1$, het$^2$, and heterocycloalkyl, described herein.

Examples of "het" include, but are not limited to, pyridine, thiophene, furan, pyrazoline, pyrimidine, 2-pyridyl, 3-pyridyl, 4-pyridyl, 2-pyrimidinyl, 4-pyrimidinyl, 5-pyrimidinyl, 3-pyridazinyl, 4-pyridazinyl, 3-pyrazinyl, 4-oxo-2-imidazolyl, 2-imidazolyl, 4-imidazolyl, 3-isoxazolyl, 4-isoxazolyl, 5-isoxazolyl, 3-pyrazolyl, 4-pyrazolyl, 5-pyrazolyl, 2-oxazolyl, 4-oxazolyl, 4-oxo-2-oxazolyl, 5-oxazolyl, 1,2,3-oxathiazole, 1,2,3-oxadiazole, 1,2,4-oxadiazole, 1,2,5-oxadiazole, 1,3,4-oxadiazole, 2-thiazolyl, 4-thiazolyl, 5-thiazolyl, 3-isothiazole, 4-isothiazole, 5-isothiazole, 2-furanyl, 3-furanyl, 2-thienyl, 3-thienyl, 2-pyrrolyl, 3-pyrrolyl, 3-isopyrrolyl, 4-isopyrrolyl, 5-isopyrrolyl, 1,2,3,-oxathiazole-1-oxide, 1,2,4-oxadiazol-3-yl, 1,2,4-oxadiazol-5-yl, 5-oxo-1,2,4-oxadiazol-3-yl, 1,2,4-thiadiazol-3-yl, 1,2,4-thiadiazol-5-yl, 1,2,5-thiadiazol-3-yl, 3-oxo-1,2,4-thiadiazol-5-yl, 1,3,4-thiadiazol-5-yl, 2-oxo-1,3,4-thiadiazol-5-yl, 1,2,3-triazol-1-yl, 1,2,4-triazol-3-yl, 1,2,4-triazol-5-yl, 1,2,3,4-tetrazol-5-yl, 5-oxazolyl, 3-isothiazolyl, 4-isothiazolyl, 5-isothiazolyl, 1,3,4,-oxadiazole, 4-oxo-2-thiazolinyl, 5-methyl-1,3,4-thiadiazol-2-yl, thiazoledione, 1,2,3,4-thiatriazole, 1,2,4-dithiazolone, phthalimide, quinolinyl, morpholinyl, benzoxazoyl, diazinyl, triazinyl, quinolinyl, quinoxalinyl, naphthyridinyl, azetidinyl, pyrrolidinyl, hydantoinyl, oxathiolanyl, dioxolanyl, imidazolidinyl, and azabicyclo[2.2.1]heptyl.

The term "heteroaryl" refers to an aromatic het, examples of which include, but are not limited to, pyridine and thiophene.

The term "substituted alkyl" refers to an alkyl moiety including 1–4 substituents selected from halo, het, cycloalkyl, cycloalkenyl, aryl, —OQ$_{10}$, —SQ$_{10}$, —S(O)$_2$Q$_{10}$, —S(O)Q$_{10}$, —OS(O)$_2$Q$_{10}$, —C(=NQ$_{10}$)Q$_{10}$, —C(=NOQ$_{10}$)Q$_{10}$, —SC(O)Q$_{10}$, —NQ$_{10}$Q$_{10}$, —C(O)Q$_{10}$, —C(S)Q$_{10}$, —C(O)OQ$_{10}$, —OC(O)Q$_{10}$, —C(O)NQ$_{10}$Q$_{10}$, —C(O)C(Q$_{16}$)$_2$OC(O)Q$_{10}$, —CN, =O, =S, —NQ$_{10}$C(O)Q$_{10}$, —NQ$_{10}$C(O)NQ$_{10}$Q$_{10}$, —S(O)$_2$NQ$_{10}$Q$_{10}$, —NQ$_{10}$S(O)$_2$Q$_{10}$, —NQ$_{10}$S(O)Q$_{10}$, —NQ$_{10}$SQ$_{10}$, —NO$_2$, and —SNQ$_{10}$Q$_{10}$. Each of the het, cycloalkyl, cycloalkenyl, and aryl may be optionally substituted with 1–4 substituents independently selected from halo and Q$_{15}$.

The term "substituted aryl" refers to an aryl moiety having 1–3 substituents selected from —OQ$_{10}$, —SQ$_{10}$, —S(O)$_2$Q$_{10}$, —S(O)Q$_{10}$, —OS(O)$_2$Q$_{10}$, —C(=NQ$_{10}$)Q$_{10}$, —SC(O)Q$_{10}$, —NQ$_{10}$Q$_{10}$, —C(O)Q$_{10}$, —C(S)Q$_{10}$, —C(O)OQ$_{10}$, —OC(O)Q$_{10}$, —C(O)NQ$_{10}$Q$_{10}$, —C(O)C(Q$_{16}$)$_2$OC(O)Q$_{10}$, —CN, —NQ$_{10}$C(O)Q$_{10}$, —NQ$_{10}$C(O)NQ$_{10}$Q$_{10}$, —S(O)$_2$NQ$_{10}$Q$_{10}$, —NQ$_{10}$S(O)$_2$Q$_{10}$, —NQ$_{10}$S(O)Q$_{10}$, —NQ$_{10}$SQ$_{10}$, —NO$_2$, —SNQ$_{10}$Q$_{10}$, alkyl, substituted alkyl, het, halo, cycloalkyl, cycloalkenyl, and aryl. The het, cycloalkyl, cycloalkenyl, and aryl may be optionally substituted with 1–3 substituents selected from halo and Q$_{15}$.

The term "substituted het" refers to a het moiety including 1–4 substituents selected from —OQ$_{10}$, —SQ$_{10}$, —S(O)$_2$Q$_{10}$, —S(O)Q$_{10}$, —OS(O)$_2$Q$_{10}$, —C(=NQ$_{10}$)Q$_{10}$, —C(=NOQ$_{10}$)Q$_{10}$, —SC(O)Q$_{10}$, —NQ$_{10}$Q$_{10}$, —C(O)Q$_{10}$, —C(S)Q$_{10}$, —C(O)OQ$_{10}$, —OC(O)Q$_{10}$, —C(O)NQ$_{10}$Q$_{10}$, —C(O)C(Q$_{16}$)$_2$OC(O)Q$_{10}$, —CN, —NQ$_{10}$C(O)Q$_{10}$, —NQ$_{10}$C(O)NQ$_{10}$Q$_{10}$, —S(O)$_2$NQ$_{10}$Q$_{10}$, —NQ$_{10}$S(O)$_2$Q$_{10}$, —NQ$_{10}$S(O)Q$_{10}$, —NQ$_{10}$SQ$_{10}$, —NO$_2$, —SNQ$_{10}$Q$_{10}$, alkyl, substituted alkyl, het, halo, cycloalkyl, cycloalkenyl, and aryl. The substituted het also may be substituted by one or more =O or =S substituents provided that the O or S are bound to ring atoms capable of supporting a double bond between the ring atom and O or S. The het, cycloalkyl, cycloalkenyl, and aryl may be optionally substituted with 1–3 substituents selected from halo and Q$_{15}$.

The term "substituted alkenyl" refers to a alkenyl moiety including 1–3 substituents —OQ$_{10}$, —SQ$_{10}$, —S(O)$_2$Q$_{10}$, —S(O)Q$_{10}$, —OS(O)$_2$Q$_{10}$, —C(=NQ$_{10}$)Q$_{10}$, —C(=NOQ$_{10}$)Q$_{10}$, —SC(O)Q$_{10}$, —NQ$_{10}$Q$_{10}$, —C(O)Q$_{10}$, —C(S)Q$_{10}$, —C(O)OQ$_{10}$, —OC(O)Q$_{10}$, —C(O)NQ$_{10}$Q$_{10}$, —C(O)C(Q$_{16}$)$_2$OC(O)Q$_{10}$, —CN, =O, =S, —NQ$_{10}$C(O)Q$_{10}$, —NQ$_{10}$C(O)NQ$_{10}$Q$_{10}$, —S(O)$_2$NQ$_{10}$Q$_{10}$, —NQ$_{10}$S(O)$_2$Q$_{10}$, —NQ$_{10}$S(O)Q$_{10}$, —NQ$_{10}$SQ$_{10}$, —NO$_2$, —SNQ$_{10}$Q$_{10}$, alkyl, substituted alkyl, het, halo, cycloalkyl, cycloalkenyl, and aryl. The het, cycloalkyl, cycloalkenyl, and aryl may be optionally substituted with 1–3 substituents selected from halo and Q$_{15}$.

The term "substituted alkoxy" refers to an alkoxy moiety including 1–3 substituents —OQ$_{10}$, —SQ$_{10}$, —S(O)$_2$Q$_{10}$, —S(O)Q$_{10}$, —OS(O)$_2$Q$_{10}$, —C(=NQ$_{10}$)Q$_{10}$, —SC(O)Q$_{10}$, —NQ$_{10}$Q$_{10}$, —C(O)Q$_{10}$, —C(S)Q$_{10}$, —C(O)OQ$_{10}$, —OC(O)Q$_{10}$, —C(O)NQ$_{10}$Q$_{10}$, —C(O)C(Q$_{16}$)$_2$OC(O)Q$_{10}$, —CN, =O, =S, —NQ$_{10}$C(O)Q$_{10}$, —NQ$_{10}$C(O)NQ$_{10}$Q$_{10}$, —S(O)$_2$NQ$_{10}$Q$_{10}$, —NQ$_{10}$S(O)$_2$Q$_{10}$, —NQ$_{10}$S(O)Q$_{10}$, —NQ$_{10}$SQ$_{10}$, —NO$_2$, —SNQ$_{10}$Q$_{10}$, alkyl, substituted alkyl, het, halo, cycloalkyl, cycloalkenyl, and aryl. The het, cycloalkyl, cycloalkenyl, and aryl may be optionally substituted with 1–3 substituents selected from halo and Q$_{15}$.

The term "substituted cycloalkenyl" refers to a cycloalkenyl moiety including 1–3 substituents —OQ$_{10}$, —SQ$_{10}$, —S(O)$_2$Q$_{10}$, —S(O)Q$_{10}$, —OS(O)$_2$Q$_{10}$, —C(=NQ$_{10}$)Q$_{10}$, —SC(O)Q$_{10}$, —NQ$_{10}$Q$_{10}$, —C(O)Q$_{10}$, —C(S)Q$_{10}$, —C(O)OQ$_{10}$, —OC(O)Q$_{10}$, —C(O)NQ$_{10}$Q$_{10}$, —C(O)C(Q$_{16}$)$_2$OC(O)Q$_{10}$, —CN, =O, =S, —NQ$_{10}$C(O)Q$_{10}$, —NQ$_{10}$C(O)NQ$_{10}$Q$_{10}$, —S(O)$_2$NQ$_{10}$Q$_{10}$, —NQ$_{10}$S(O)$_2$Q$_{10}$, —NQ$_{10}$S(O)Q$_{10}$, —NQ$_{10}$SQ$_{10}$, —NO$_2$, —SNQ$_{10}$Q$_{10}$, alkyl, substituted alkyl, het, halo, cycloalkyl, cycloalkenyl, and aryl. The het, cycloalkyl, cycloalkenyl, and aryl may be optionally substituted with 1–3 substituents selected from halo and Q$_{15}$.

The term "substituted amino" refers to an amino moiety in which one or both of the amino hydrogens are replaced with a group selected from —OQ$_{10}$, —SQ$_{10}$, —S(O)$_2$Q$_{10}$, —S(O)Q$_{10}$, —OS(O)$_2$Q$_{10}$, —C(O)Q$_{10}$, —C(S)Q$_{10}$, —C(O)OQ$_{10}$, —OC(O)Q$_{10}$, —C(O)NQ$_{10}$Q$_{10}$, —C(O)C(Q$_{16}$)$_2$OC(O)Q$_{10}$, —CN, alkyl, substituted alkyl, het, halo, cycloalkyl, cycloalkenyl, and aryl. The het, cycloalkyl, cycloalkenyl, and aryl may be optionally substituted with 1–3 substituents selected from halo and Q$_{15}$.

Each Q$_{10}$ is independently selected from —H, alkyl, cycloalkyl, het, cycloalkenyl, and aryl. The het, cycloalkyl, cycloalkenyl, and aryl may be optionally substituted with 1–3 substituents selected from halo and Q$_{13}$.

Each Q$_{11}$ is independently selected from —H, halo, alkyl, aryl, cycloalkyl, and het. The alkyl, cycloalkyl, and het may be optionally substituted with 1–3 substituents independently selected from halo, —NO$_2$, —CN, =S, =O , and Q$_{14}$. The aryl may be optionally substituted with 1–3 substituents independently selected from halo, —NO$_2$, —CN, and Q$_{14}$.

Each Q$_{13}$ is independently selected from Q$_{11}$, —OQ$_{11}$, —SQ$_{11}$, —S(O)$_2$Q$_{11}$, —S(O)Q$_{11}$, —OS(O)$_2$Q$_{11}$, —C(=NQ$_{11}$)Q$_{11}$, —SC(O)Q$_{11}$, —NQ$_{11}$Q$_{11}$, —C(O)Q$_{11}$, —C(S)Q$_{11}$, —C(O)OQ$_{11}$, —OC(O)Q$_{11}$, —C(O)NQ$_{11}$Q$_{11}$, —C(O)C(Q$_{16}$)$_2$OC(O)Q$_{10}$, —CN, =O, =S, —NQ$_{11}$C(O)Q$_{11}$, —NQ$_{11}$C(O)NQ$_{11}$Q$_{11}$, —S(O)$_2$NQ$_{11}$Q$_{11}$, —NQ$_{11}$S(O)$_2$Q$_{11}$, —NQ$_{11}$S(O)Q$_{11}$, —NQ$_{11}$SQ$_{11}$, —NO$_2$, and —SNQ$_{11}$Q$_{11}$, provided that Q$_{13}$ is not =O or =S when Q$_{10}$ is aryl or a het lacking any atom capable of forming a double bond with O or S.

Each Q$_{14}$ is —H or a substituent selected from alkyl, cycloalkyl, cycloalkenyl, phenyl, or naphthyl, each optionally substituted with 1–4 substituents independently selected from —F, —Cl, —Br, —I, —OQ$_{16}$, —SQ$_{16}$, —S(O)$_2$Q$_{16}$, —S(O)Q$_{16}$, —OS(O)$_2$Q$_{16}$, —NQ$_{16}$Q$_{16}$, —C(O)Q$_{16}$, —C(S)Q$_{16}$, —C(O)OQ$_{16}$, —NO$_2$, —C(O)NQ$_{16}$Q$_{16}$, —CN, —NQ$_{16}$C(O)Q$_{16}$, —NQ$_{16}$C(O)NQ$_{16}$Q$_{16}$, —S(O)$_2$NQ$_{16}$Q$_{16}$, and —NQ$_{16}$S(O)$_2$Q$_{16}$. The alkyl, cycloalkyl, and cycloalkenyl may be further substituted with =O or =S.

Each Q$_{15}$ is alkyl, cycloalkyl, cycloalkenyl, het, phenyl, or naphthyl, each optionally substituted with 1–4 substituents independently selected from —F, —Cl, —Br, —I, —OQ$_{16}$, —SQ$_{16}$, —S(O)$_2$Q$_{16}$, —S(O)Q$_{16}$, —OS(O)$_2$Q$_{16}$, —C(=NQ$_{16}$)Q$_{16}$, —SC(O)Q$_{16}$, —NQ$_{16}$Q$_{16}$, —C(O)Q$_{16}$, —C(S)Q$_{16}$, —C(O)OQ$_{16}$, —OC(O)Q$_{16}$, —C(O)NQ$_{16}$Q$_{16}$, —C(O)C(Q$_{16}$)$_2$OC(O)Q$_{16}$, —CN, —NQ$_{16}$C(O)Q$_{16}$, —NQ$_{16}$C(O)NQ$_{16}$Q$_{16}$, —S(O)$_2$NQ$_{16}$Q$_{16}$, —NQ$_{16}$S(O)$_2$Q$_{16}$, —NQ$_{16}$S(O)Q$_{16}$, —NQ$_{16}$SQ$_{16}$, —NO$_2$, and —SNQ$_{16}$Q$_{16}$. The alkyl, cycloalkyl, and cycloalkenyl may be further substituted with =O or =S.

Each Q$_{16}$ is independently selected from —H, alkyl, and cycloalkyl. The alkyl and cycloalkyl may optionally include 1–3 halos.

Mammal refers to human or animals.

The compounds of the present invention are generally named according to the IUPAC or CAS nomenclature system. Abbreviations which are well known to one of ordinary skill in the art may be used (e.g. "Ph" for phenyl, "Me" for methyl, "Et" for ethyl, "O" for oxygen atom, "S" for sulfur atom, "N" for nitrogen atom, "h" for hour or hours and "rt" for room temperature).

The compounds of the present invention can be converted to their salts, where appropriate, according to conventional methods.

The term "pharmaceutically acceptable salts" refers to acid addition salts useful for administering the compounds of this invention and include hydrochloride, hydrobromide, hydroiodide, sulfate, phosphate, acetate, propionate, lactate, mesylate, maleate, malate, succinate, tartrate, citric acid, 2-hydroxyethyl sulfonate, fumarate and the like. These salts may be in hydrated form.

The compounds of Formula I of this invention contain a chiral center, such as at C-5 of the oxazolidinone ring, and as such there exist two enantiomers or a racemic mixture of both. This invention relates to both the enantiomer that possesses the useful properties described herein, as well as to mixtures containing both of the isomers. In addition, depending on substituents, additional chiral centers and other isomeric forms may be present in compounds of formula I, and this invention embraces all possible stereoisomers and geometric forms.

The compounds of this invention are useful for treatment of microbial infections in humans and other warm blooded animals, under both parenteral and oral administration.

The pharmaceutical compositions of this invention may be prepared by combining the compounds of this invention with a solid or liquid pharmaceutically acceptable carrier and, optionally, with pharmaceutically acceptable adjuvants and excipients employing standard and conventional techniques. Solid form compositions include powders, tablets, dispersible granules, capsules, cachets and suppositories. A solid carrier can be at least one substance which may also function as a diluent, flavoring agent, solubilizer, lubricant, suspending agent, binder, tablet disintegrating agent, and encapsulating agent. Inert solid carriers include magnesium carbonate, magnesium stearate, talc, sugar, lactose, pectin, dextrin, starch, gelatin, cellulosic materials, low melting wax, cocoa butter, and the like. Liquid form compositions include solutions, suspensions and emulsions. For example, there may be provided solutions of the compounds of this invention dissolved in water and water-propylene glycol systems, optionally containing suitable conventional coloring agents, flavoring agents, stabilizers and thickening agents.

Preferably, the pharmaceutical composition is provided employing conventional techniques in unit dosage form containing effective or appropriate amounts of the active component, that is, the compound according to this invention.

The quantity of active component, that is the compound according to this invention, in the pharmaceutical composition and unit dosage form thereof may be varied or adjusted widely depending upon the particular application, the potency of the particular compound and the desired concentration. Generally, the quantity of active component will range between 0.5% to 90% by weight of the composition.

In therapeutic use for treating, or combatting, bacterial infections in warm-blooded animals, the compounds or pharmaceutical compositions thereof will be administered orally, parenterally and/or topically at a dosage to obtain and maintain a concentration, that is, an amount, or blood-level of active component in the animal undergoing treatment which will be antibacterially effective. Generally, such antibacterially effective amount of dosage of active component will be in the range of about 0.1 to about 100, more preferably about 3.0 to about 50 mg/kg of body weight/day. It is to be understood that the dosages may vary depending upon the requirements of the patient, the severity of the bacterial infection being treated, and the particular compound being used. Also, it is to be understood that the initial dosage administered may be increased beyond the above upper level in order to rapidly achieve the desired blood-level or the initial dosage may be smaller than the optimum and the daily dosage may be progressively increased during the course of treatment depending on the particular situation. If desired, the daily dose may also be divided into multiple doses for administration, e.g., 2–4 times per day.

The compounds according to this invention may be administered parenterally, for example, by intravenous injection or by other parenteral routes of administration. Pharmaceutical compositions for parenteral administration will generally contain a pharmaceutically acceptable amount of the compound or a soluble salt (acid addition salt or base salt) dissolved in a pharmaceutically acceptable liquid carrier such as, for example, water-for-injection and a buffer to provide a suitably buffered isotonic solution, for example, having a pH of about 3.5–6. Suitable buffering agents include, for example, trisodium orthophosphate, sodium bicarbonate, sodium citrate, N-methylglucamine, L(+)-lysine and L(+)-arginine to name but a few representative buffering agents. The compounds of this invention generally will be dissolved in the carrier in an amount sufficient to provide a pharmaceutically acceptable injectable concentration in the range of about 1 mg/mL to about 400 mg/mL of solution. The resulting liquid pharmaceutical composition will be administered so as to obtain the above-mentioned antibacterially effective amount of dosage. The compounds according to this invention are advantageously administered orally in solid and liquid dosage forms.

As a topical treatment an effective amount of Formula I is admixed in a pharmaceutically acceptable gel or cream vehicle that can be applied to the patient's skin at the area of treatment. Preparation of such creams and gels is well known in the art and can include penetration enhancers.

The oxazolidinone antibacterial agents of this invention have useful activity against a variety of organisms. The in vitro activity of compounds of this invention can be assessed by standard testing procedures such as the determination of minimum inhibitory concentration (MIC) by agar dilution as described in "Approved Standard. Methods for Dilution Antimicrobial Susceptibility Tests for Bacteria That Grow Aerobically", 3rd. ed., published 1993 by the National Committee for Clinical Laboratory Standards, Villanova, Pa., USA.

Compounds of formula I may be produced by methods known to those skilled in the art. For instance, the compounds of formula I may be synthesized via Scheme I as shown below.

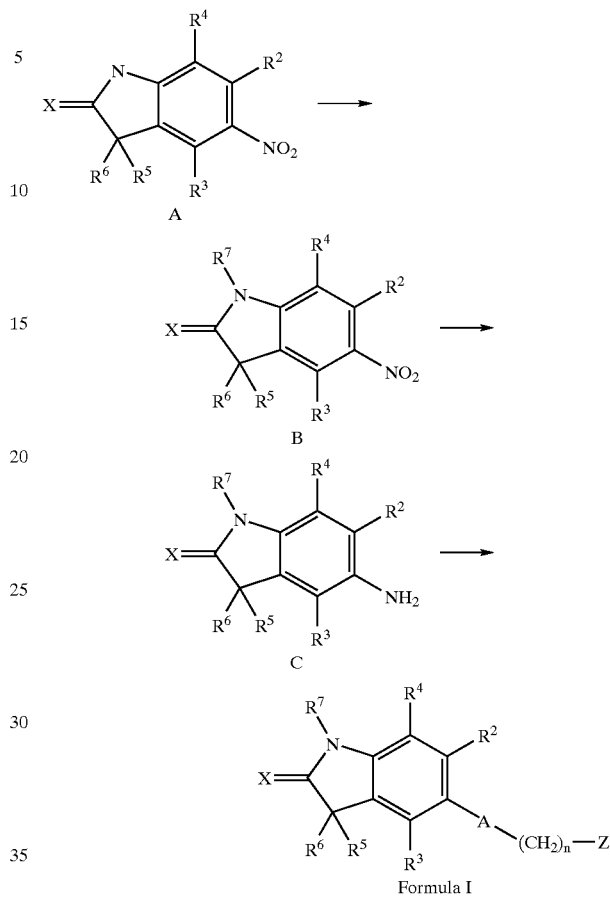

Scheme I

Formula I

Referring to Scheme I, a functionalized nitro-oxindole A (X=O) is alkylated with an alkyl halide or sulfonate ester in the presence of a base such as 1,8-diazobicyclo[5.4.0]undec-7-ene (DBU) or potassium carbonate to form an oxindole B. Reduction of the nitro group of B using, for example, catalytic hydrogenation over a palladium or platinum catalyst affords the amino-oxindole C. Conversion of the amino-oxindole C to the compounds of this invention can be achieved by known methods or as outlined in the schemes below. For example, as outlined in Scheme II, the amino-oxindole C may be treated with an alkylchloroformate in the presence of an appropriate base, such as sodium bicarbonate, to give the carbamate intermediate D. Subsequent treatment with 2(S)-acetylamino-1-(chloromethyl)ethyl acetate (*Tet. Lett.* 1996, 37(44), 7937–7940) in the presence of a base such as lithium t-butoxide in a solvent such as dimethylformamide at temperatures of about 0° C. to 25° C. then gives the 5-(acetylaminomethyl)oxazolidinone oxindole E (W=O, $R^1$=methyl)

A more general synthesis of these 5-(acylaminomethyl) oxazolidinone oxindoles is also shown in Scheme II starting from the carbamate D. Treatment with a lithium base such as n-butyllithium or lithium hexamethyldisilazide in a solvent such as tetrahydrofuran at a temperature typically in a range from −78° C. to −40° C. affords the lithiated species which is directly treated with (R)-glycidyl butyrate and warmed to room temperature to give the 5-(hydroxymethyl) oxazolidinone oxindole F. The hydroxy group is then converted to a suitable leaving group (Lg) such as an alkyl or aryl sulfonate using alkyl- or arylsulfonyl chloride reagents in the presence of an acid-scavenging amine such as triethylamine in a solvent such as dichloromethane or tetrahydrofuran. The leaving group is then displaced with an azide salt (e.g., sodium azide) in a solvent such as acetone or dimethyl sulfoxide at a temperature generally in the range of about 25° C. to 75° C., and the alkyl azide produced in then reduced to give the 5-(aminomethyl)oxazolidinone intermediate H. This can be accomplished, for example, by catalytic hydrogenation or through reaction of the azide with triphenylphosphine in a solvent such as tetrahydrofuran to give an iminophosphorane that is then hydrolyzed to the amine at temperatures of about 20° C. to 60° C. upon addition of water. The amine is then acylated (W=O) or thioacylated (W=S) using methods known to one skilled in the art to give the target structure E.

compounds F (described in the previous scheme) and conversion of these intermediates to the final compounds I is known art (see Gravestock, M. B., International Publications WO 99/64417 and WO 00/21960). First, the hydroxy group is converted to a displaceable group (Lg) such as alkyl or aryl sulfonate, bromide, or iodide. This activation may be accomplished according to procedures known to those skilled in the art and as described in Scheme II. Then, the activated hydroxy compound is reacted with a compound of the formula HN(Pg)het¹, HOhet¹, HShet¹ or the corresponding metal alkoxide salts M-N(Pg)het¹, M-Ohet¹, M-Shet¹ where M is an alkali metal or another metal known to promote O-alkylation (e.g., silver) and "Pg" is a suitable protecting group. Alternatively, the hydroxymethyl starting material may be reacted directly with compounds of the formula HN(Pg)het¹, HOhet¹, HShet¹ under Mitsunobu-

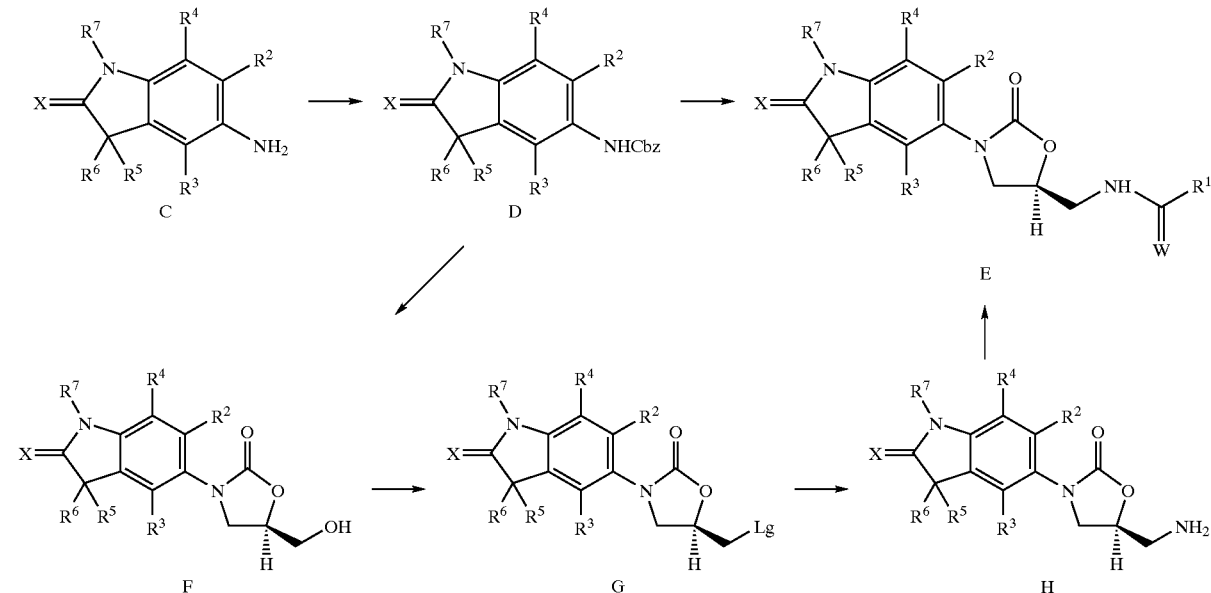

Scheme III below describes general methods for the preparation of compounds of Formula I in which A=oxazolidinone, n=1 and Z=NHhet¹, Ohet¹ or Shet¹. The starting materials for this procedure are the hydroxymethyl compounds F (described in the previous scheme) and conversion of these intermediates to the final compounds I is type activation in the presence, for example, of free or polymer-bound triphenylphosphine and diethyl (or diisopropyl) azodicarboxylate. As a final step, removal of the protecting group using known methods is carried out.

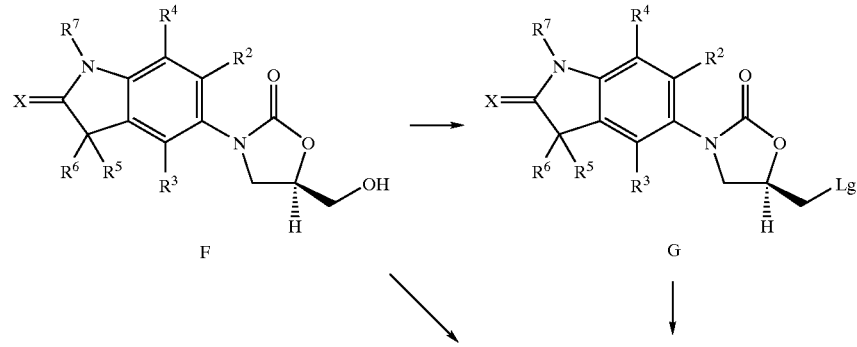

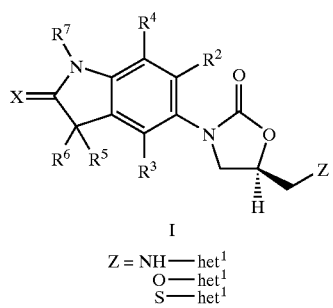

$Z = NH—het^1$
$O—het^1$
$S—het^1$

Scheme IV below describes selected methods for the preparation of compounds of Formula I in which A=oxazolidinone, n=1 and Z=het². Preparation of these analogs from the activated hydroxymethyl oxazolidinones G is known art (see Gravestock, M. B., Betts, M. J., and Griffin, D. A., International Publications WO 01/81350). Structure G can simply be reacted with het²-H in the free base form or as the anion het²—formed from the free base to give the target structure J. An alternate method for 1,2,3-triazoles (i.e., structure L) involves conversion of structure G to the azide K (as described in Scheme II) followed by cycloaddition with norbornadiene. See also International Publications WO 99/64417 and WO 00/21960, along with WO 01/81350, for additional routes to structure J.

two-step procedure. First, treatment with an alkyl (2R)-epoxypropanoate (or glycidate) and lithium triflate in a suitable solvent such as acetonitrile at a suitable temperature, typically in a range from 20° C. to 110° C. depending on the solvent, affords the amino alcohol intermediate resulting from addition of the aniline nitrogen to the terminal carbon of the epoxide ring. Subsequent treatment with 1,1'-carbonyldiimidazole in a solvent such as acetonitrile or THF at an appropriate temperature, typically in a range of 20° C. to 60° C., or with phosgene in a solvent such as toluene or methylene chloride, or mixtures thereof, in the presence of a base such as triethylamine at an appropriate temperature, typically in a range from −10° C. to 25° C., then gives the oxazolidinone intermediate M ($R^8=C_{1-4}$

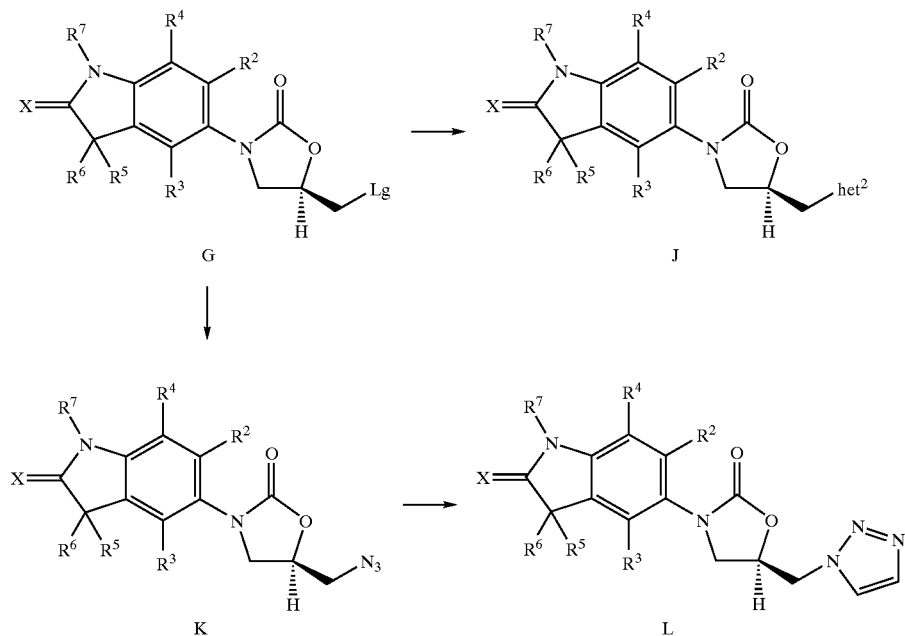

Scheme IV

Scheme V illustrates a general method for preparing compounds of Formula I where A=oxazolidinone, n=0 and Z=C(=O)NHR¹. Anilines C (see Scheme I) can be converted to the alkyl oxazolidinone-5-carboxylate M in a alkyl). This structure can then be converted to the target structure N using methods well known to one skilled in the art, for example by reaction with amines or amine derivatives ($R_1NH_2$) in a suitable solvent such as methanol.

Scheme V

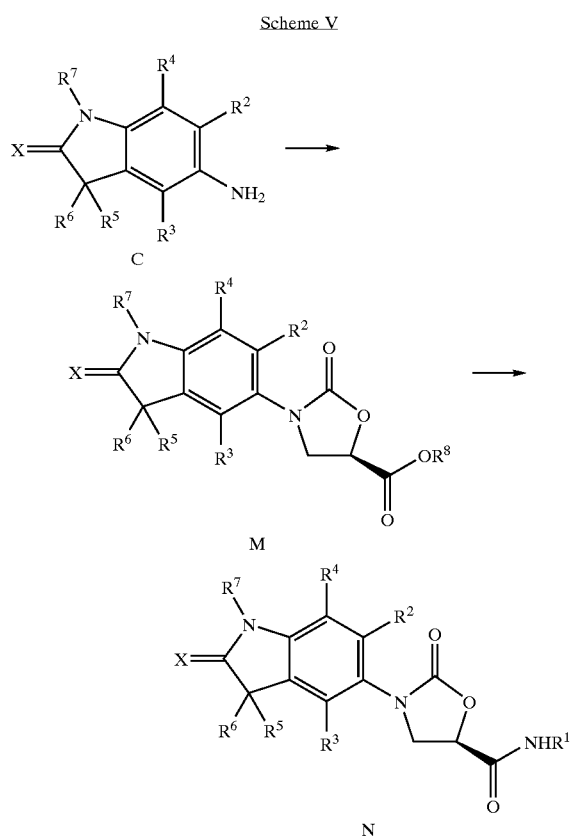

Suitable intermediates useful in preparing compounds of Formula I and additional synthetic methods to assist in producing compounds of Formula I may be found, for example, in the following publications each of which is hereby incorporated by reference.

U.S. Pat. No. 5,164,510; PCT Application and publications WO95/07271, WO00/21960, WO 9940094, WO 99/64417, WO 99/64416, WO 00/21960, and WO 01/81350; European Patent No. EP 738726 and German Patent No. DE 19802239.

Examples of compounds of the invention include, but are not limited to,
(5R)-(−)-3-(3,3-Difluoro-2,3-dihydro-1-methyl-2-oxo-1H-indol-5-yl)-N-methyl-2-oxo-5-oxazolidinecarboxamide;
(5R)-(−)-3-(3,3-difluoro-2,3-dihydro-1-methyl-2-oxo-1H-indol-5-yl)-2-oxo-5-oxazolidinecarboxamide;
(5R)-(−)-3-(3,3-difluoro-2,3-dihydro-1-ethyl-2-oxo-1H-indol-5-yl)-2-oxo-5-oxazolidinecarboxamide;
(5R)-(−)-3-(3,3-Difluoro-2,3-dihydro-1-ethyl-2-oxo-1H-indol-5-yl)-N-methyl-2-oxo-5-oxazolidinecarboxamide;
N-[[(5S)-(−)-3-(3,3-Difluoro-2,3-dihydro-1-methyl-2-oxo-1H-indol-5-yl)-2-oxo-5-oxazolidinyl]methyl]acetamide; and
N-[[(5S)-(−)-3-(3,3-Difluoro-2,3-dihydro-1-ethyl-2-oxo-1H-indol-5-yl)-2-oxo-5-oxazolidinyl]methyl]acetamide.

In some embodiments, the antibacterial compounds are prodrugs of the compounds of formula I. The expression "prodrug" denotes a derivative of a known direct acting drug, which is transformed into the active drug by an enzymatic or chemical process. Prodrugs of the compounds of formula I are prepared by modifying functional groups present on the compound in such a way that the modifications are cleaved, either in routine manipulation or in vivo, to the parent compound. Prodrugs include, but are not limited to, compounds of structure (I) wherein hydroxy, amine or sulfhydryl groups are bonded to any group that, when administered to the animal, cleaves to form the free hydroxyl, amino or sulfhydryl group, respectively. Representative examples of prodrugs include, but are not limited to, acetate, formate and benzoate derivatives of alcohol and amine functional groups. See Notari, R. E., "Theory and Practice of Prodrug Kinetics," Methods in Enzymology, 112:309–323 (1985); Bodor, N., "Novel Approaches in Prodrug Design," Drugs of the Future, 6(3):165–182 (1981); and Bundgaard, H., "Design of Prodrugs: Bioreversible-Derivatives for Various Functional Groups and Chemical Entities," in Design of Prodrugs (H. Bundgaard, ed.), Elsevier, N.Y. (1985).

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

Example 1

(5R)-(−)-3-(3,3-Difluoro-2,3-dihydro-1-methyl-2-oxo-1H-indol-5-yl)-N-methyl-2-oxo-5-oxazolidinecarboxamide

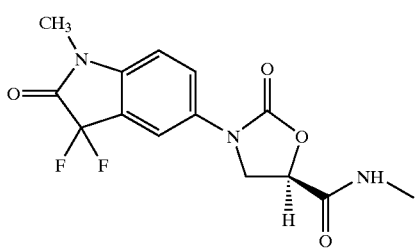

Step 1: Preparation of 3,3-difluoro-1-methyl-5-nitro-1,3-dihydro-2H-indol-2-one

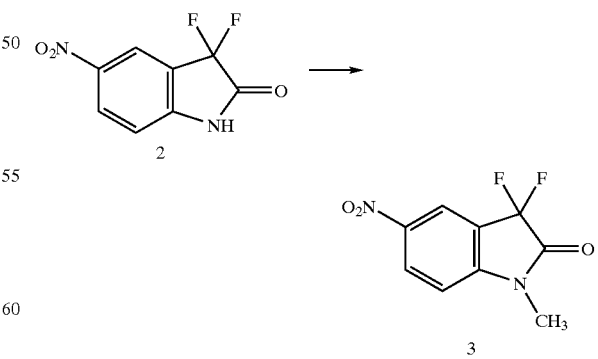

A solution of 3,3-difluoro-5-nitro-1,3-dihydro-2H-indol-2-one 2 (Tetrahedron, 1999, 55, 1881–92, 7.05 g, 32.9 mmol) in anhydrous N,N-dimethylformamide (66 mL) under $N_2$ is treated with 1,8-diazabicyclo[5.4.0]undec-7-ene (6.40 mL, 42.8 mmol) dropwise followed by iodomethane (2.46 mL, 39.5 mmol). Following a slight exotherm, the reaction mixture is stirred at ambient temperature for 18 h, diluted with ice-water (100 mL) and filtered to give the title compound 3, mp 131.5–134.5° C.

Step 2: Preparation of 5-amino-3,3-difluoro-1-methyl-1,3-dihydro-2H-indol-2-one

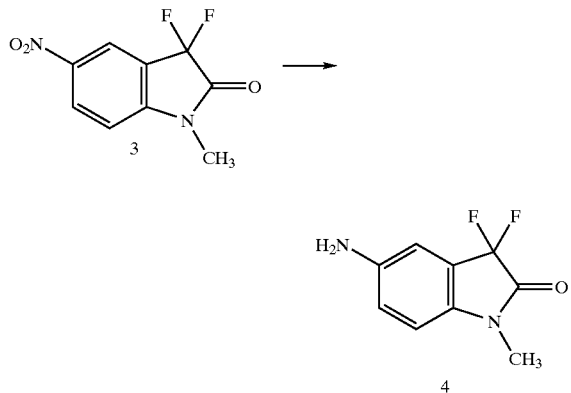

A mixture of 3,3-difluoro-1-methyl-5-nitro-1,3-dihydro-2H-indol-2-one 3 (Step 1, 3.80 g, 16.6 mmol) and platinum oxide (188 mg, 0.828 mmol, 5 mol %) in 1:1 THF/MeOH (100 mL) is shaken on a Parr apparatus under a 20 psi hydrogen atmosphere for 1.5 h. The catalyst is then removed by filtration through a pad of Celite, and the filtrate is concentrated under reduced pressure to give the title compound 4, MS (ESI+) for $C_9H_8N_2OF_2$ m/z 199 $(M+H)^+$, which can be used without further purification. Purification by silica gel chromatography (40% EtOAc/heptane eluent) provides an analytical sample, mp 186–9° C.

Step 3: Preparation of butyl (5R)-3-(3,3-difluoro-2,3-dihydro-1-methyl-2-oxo-1H-indol-5-yl)-2-oxo-5-oxazolidinecarboxylate

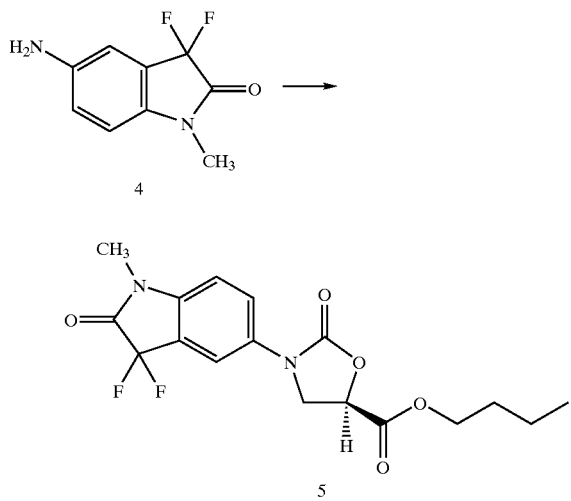

A mixture of 5-amino-3,3-difluoro-1-methyl-1,3-dihydro-2H-indol-2-one 4 (Step 2, 4.50 g, 22.7 mmol) and butyl (2R)-glycidate (3.60 g, 25.0 mmol) in dry acetonitrile (11.4 mL) under $N_2$ is heated to 70° C. with vigorous stirring and treated with lithium trifluoromethanesulfonate (3.89 g, 25.0 mmol) all at once. The resulting mixture is heated to gentle reflux, refluxed for 1.5 h and then concentrated under reduced pressure. The product mixture is taken up in 10% MeOH/CH$_2$Cl$_2$ (150 mL), washed with water (100 mL) and saline (50 mL), dried over anhydrous sodium sulfate and concentrated under reduced pressure to give the crude amino alcohol intermediate [MS (ESI+) for $C_{16}H_{20}N_2O_4F_2$ m/z 343 $(M+H)^+$] which is used without further purification. A solution of this intermediate in dry acetonitrile (113 mL) under $N_2$ is treated with 1,1'-carbonyldiimidazole (5.52 g, 34.1 mmol), and the reaction is stirred at ambient temperature for 24 h. Solvent is removed under reduced pressure, and the residue is taken up in CH$_2$Cl$_2$ (125 mL), washed with aqueous hydrochloric acid (0.2 M, 3×50 mL) and saline (50 mL), dried over anhydrous sodium sulfate, concentrated under reduced pressure and chromatographed on two Biotage Flash 40M 90 g silica gel cartridges, eluting with EtOAc/CH$_2$Cl$_2$ (3/97). Pooling and concentration of those fractions with an $R_f$=0.40 by TLC (EtOAc/hexanes, 50/50) gives the title compound 5, MS (ESI+) for $C_{17}H_{18}N_2O_5F_2$ m/z 369 $(M+H)^+$; $^1$H NMR (400 MHz, DMSO-d$_6$) δ 7.96 (m, 1H), 7.76 (dd, 1H), 7.28 (d, 1H), 5.34 (dd, 1H), 4.41 (t, 1H), 4.18 (m, 3H), 3.19 (s, 3H), 1.62 (quint, 2H), 1.35 (sext, 2H), 0.90 (t, 3H).

Step 4: Preparation of (5R)-(−)-3-(3,3-difluoro-2,3-dihydro-1-methyl-2-oxo-1H-indol-5-yl)-N-methyl-2-oxo-5-oxazolidinecarboxamide

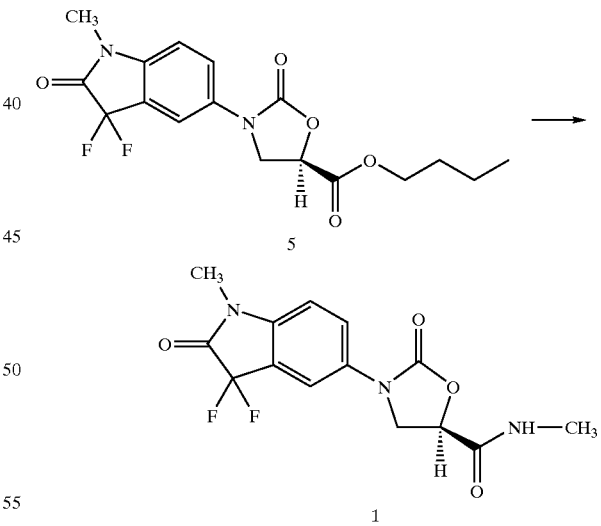

Butyl (5R)-3-(3,3-difluoro-2,3-dihydro-1-methyl-2-oxo-1H-indol-5-yl)-2-oxo-5-oxazolidinecarboxylate 5 (Step 3, 5.55 g, 15.1 mmol) is treated with 2M MeNH$_2$ in MeOH (151 mL) with vigorous stirring. The resulting slurry is stirred at ambient temperature for 1 h, and the precipitated product is isolated by filtration to give the title compound 1, mp 242.5–245° C.; MS (ESI+) for $C_{14}H_{13}N_3O_4F_2$ m/z 326 $(M+H)^+$; $[\square]^{25}_D$ −39 (c 0.95, DMSO).

Example 2

(5R)-(−)-3-(3,3-difluoro-2,3-dihydro-1-methyl-2-oxo-1H-indol-5-yl)-2-oxo-5-oxazolidinecarboxamide

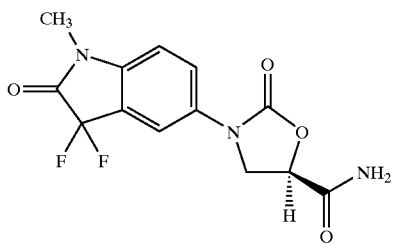

Butyl (5R)-3-(3,3-difluoro-2,3-dihydro-1-methyl-2-oxo-1H-indol-5-yl)-2-oxo-5-oxazolidinecarboxylate 5 (EXAMPLE 1, Step 4, 340 mg, 0.923 mmol) is treated with 7N $NH_3$ in MeOH (9.2 mL) with vigorous stirring. The resulting slurry is stirred at ambient temperature for 1 h, diluted with diethyl ether (5 mL) and the precipitated product is isolated by filtration to give the title compound 6, mp 274–7° C. (dec.); MS (ESI−) for $C_{13}H_{11}N_3O_4F_2$ m/z 310 (M−H)⁻; $[\alpha]^{25}_D$ −22 (c 0.95, DMSO).

Example 3

(5R)-(−)-3-(3,3-difluoro-2,3-dihydro-1-ethyl-2-oxo-1H-indol-5-yl)-2-oxo-5-oxazolidinecarboxamide

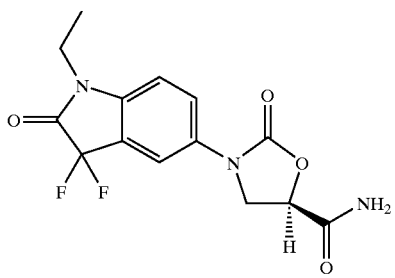

Step 1: Preparation of 3,3-difluoro-1-ethyl-5-nitro-1,3-dihydro-2H-indol-2-one

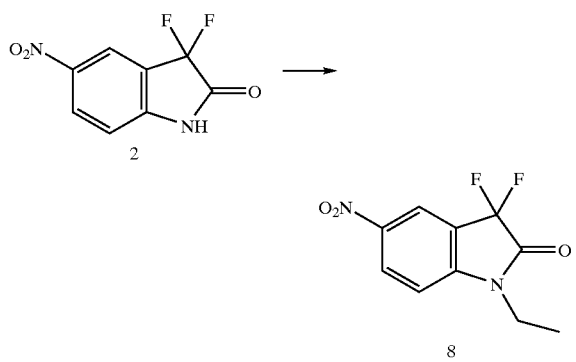

Following the general procedure of EXAMPLE 1, Step 1, and making non-critical variations but substituting iodoethane for iodomethane, the title compound 8 is obtained, mp 111–2° C.

Step 2: Preparation of 5-amino-3,3-difluoro-1-ethyl-1,3-dihydro-2H-indol-2-one

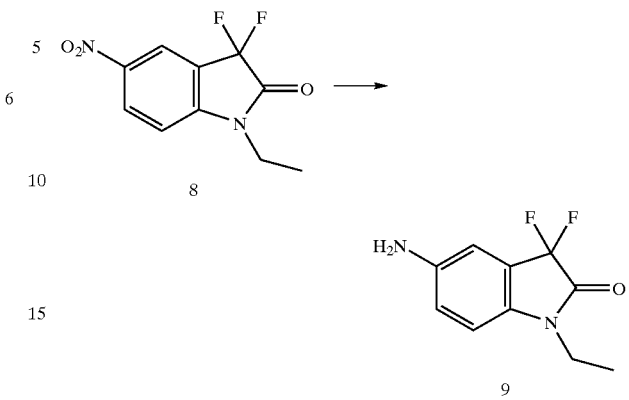

Following the general procedure of EXAMPLE 1, Step 2, and making non-critical variations but substituting 3,3-difluoro-1-ethyl-5-nitro-1,3-dihydro-2H-indol-2-one 8 for 3,3-difluoro-1-methyl-5-nitro-1,3-dihydro-2H-indol-2-one 3, the title compound 9 is obtained, mp 124–7° C.; MS (ESI+) for $C_{10}H_{10}N_2OF_2$ m/z 213 (M+H)⁺.

Step 3: Preparation of butyl (5R)-3-(3,3-difluoro-2,3-dihydro-1-ethyl-2-oxo-1H-indol-5-yl)-2-oxo-5-oxazolidinecarboxylate

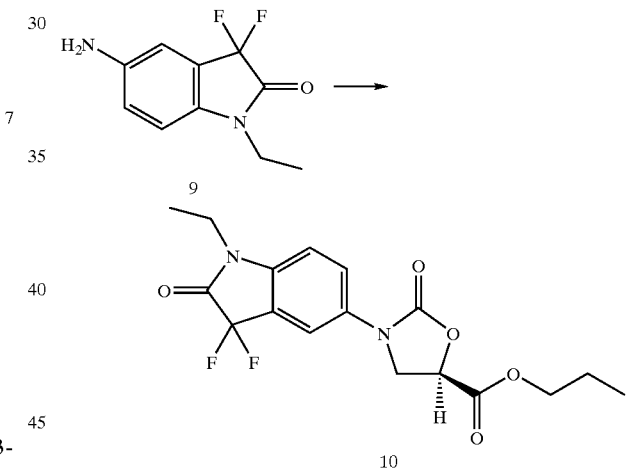

A mixture of 5-amino-3,3-difluoro-1-ethyl-1,3-dihydro-2H-indol-2-one 9 (Step 2, 715 mg, 3.37 mmol) and butyl (2R)-glycidate (729 mg, 5.05 mmol) in dry acetonitrile (13.5 mL) under $N_2$ is treated with lithium trifluoromethanesulfonate (788 mg, 5.05 mmol). The resulting mixture is heated to 75° C., stirred at this temperature for 20 h and then concentrated under reduced pressure. The product mixture is taken up in 10% MeOH/$CH_2Cl_2$ (40 mL), washed with water (20 mL) and saline (20 mL), dried over anhydrous sodium sulfate and concentrated under reduced pressure to give the crude amino alcohol intermediate [MS (ESI+) for $C_{17}H_{22}N_2O_4F_2$ m/z 357 (M+H)⁺] which is used without further purification. A solution of this intermediate in dry acetonitrile (34 mL) under $N_2$ is treated with 1,1'-carbonyldiimidazole (820 mg, 5.05 mmol), and the reaction is stirred at ambient temperature for 4 days. Solvent is removed under reduced pressure, and the residue is taken up in $CH_2Cl_2$ (50 mL), washed with aqueous hydrochloric acid (0.1 M, 2×25 mL) and saline (25 mL), dried over anhydrous sodium sulfate, concentrated under reduced pressure and chromatographed on a Biotage Flash 40M 90 g silica gel cartridges, eluting with EtOAc/CH$_2$Cl$_2$ (5/95). Pooling and concentration of those fractions with an R$_f$=0.48 by TLC (EtOAc/hexanes, 50/50) gives the title compound 10, MS (ESI+) for C$_{18}$H$_{20}$N$_2$O$_5$F$_2$ m/z 383 (M+H)$^+$; $^1$H NMR (400 MHz, DMSO-d$_6$) δ7.96 (m, 1H), 7.75 (dd, 1H), 7.35 (d, 1H), 5.34 (dd, 1H), 4.41 (t, 1H), 4.18 (m, 3H), 3.75 (q, 2H), 1.62 (quint, 2H), 1.35 (sext, 2H), 1.18 (t, 3H), 0.90 (t, 3H).

Step 4: Preparation of (5R)-(−)-3-(3,3-difluoro-2,3-dihydro-1-ethyl-2-oxo-1H-indol-5-yl)-2-oxo-5-oxazolidinecarboxamide

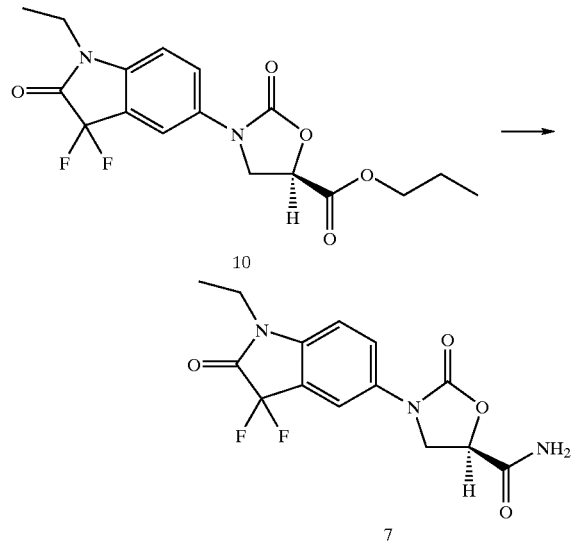

A solution of butyl (5R)-3-(3,3-difluoro-2,3-dihydro-1-ethyl-2-oxo-1H-indol-5-yl)-2-oxo-5-oxazolidinecarboxylate 10 (Step 3, 440 mg, 1.15 mmol) in MeOH (5 mL) is treated with 2M NH$_3$ in MeOH (11.5 mL), and the mixture is stirred at ambient temperature for 1 h. The solvent is removed under reduced pressure, and the product mixture is chromatographed on a Biotage Flash 40S 40 g silica gel cartridge, eluting with MeOH/CH$_2$Cl$_2$ (2/98). Pooling and concentration of those fractions having an R$_f$-0.35 by TLC (MeOH/CHCl$_3$, 10/90) and trituration and filtration from CH$_2$Cl$_2$/Et$_2$O gives the title compound 7, mp 201–3° C.; MS (ESI+) for C$_{14}$H$_{13}$N$_3$O$_4$F$_2$ m/z 326 (M+H)$^+$; [α]$^{25}_D$−20 (c 0.94, DMSO).

Example 4

(5R)-(−)-3-(3,3-Difluoro-2,3-dihydro-1-ethyl-2-oxo-1H-indol-5-yl)-N-methyl-2-oxo-5-oxazolidinecarboxamide

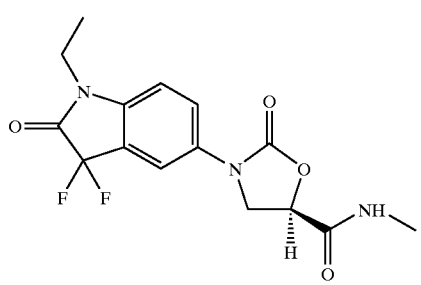

Following the general procedure of EXAMPLE 1, Step 4, and making non-critical variations but substituting butyl (5R)-3-(3,3-difluoro-2,3-dihydro-1-ethyl-2-oxo-1H-indol-5-yl)-2-oxo-5-oxazolidinecarboxylate 10 (EXAMPLE 3, Step 3) for butyl (5R)-3-(3,3-difluoro-2,3-dihydro-1-methyl-2-oxo-1H-indol-5-yl)-2-oxo-5-oxazolidinecarboxylate 5, the title compound 11 is obtained, mp 211–213° C.; MS (ESI+) for C$_{15}$H$_{15}$N$_3$O$_4$F$_2$ m/z 340 (M+H)$^+$; [α]$^{25}_D$−36 (c 1.02, DMSO).

Example 5

N-[[(5S)-(−)-3-(3,3-Difluoro-2,3-dihydro-1-methyl-2-oxo-1H-indol-5-yl)-2-oxo-5-oxazolidinyl]methyl]acetamide

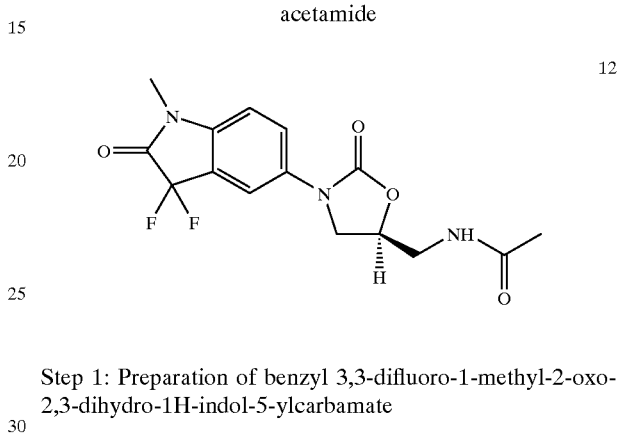

Step 1: Preparation of benzyl 3,3-difluoro-1-methyl-2-oxo-2,3-dihydro-1H-indol-5-ylcarbamate

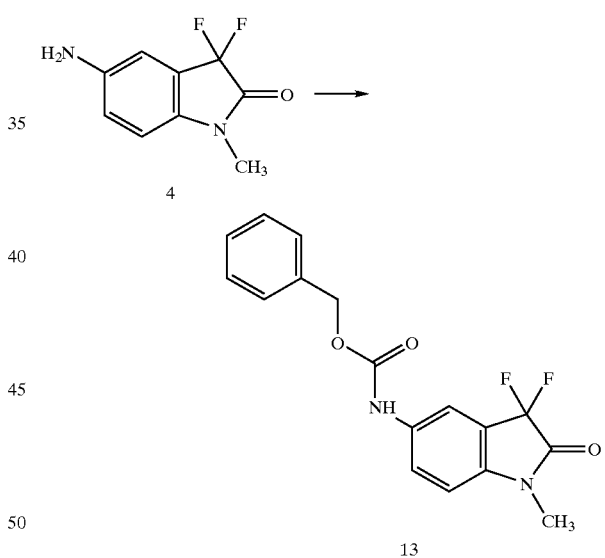

A mixture of 5-amino-3,3-difluoro-1-methyl-1,3-dihydro-2H-indol-2-one 4 (EXAMPLE 1, Step 2, 300 mg, 1.51 mmol) in THF/H$_2$O (2:1, 7.5 mL) is treated with sodium bicarbonate (254 mg, 3.02 mmol) followed by benzyl chloroformate (226 μL, 1.59 mmol), and the biphasic mixture is stirred at ambient temperature for 18 h. The reaction is diluted with H$_2$O (10 mL) and extracted with EtOAc (20 mL), and the organic phase is washed with H$_2$O (10 mL) and saline (10 mL), dried over anhydrous magnesium sulfate and concentrated under reduced pressure. The residue is recrystallized from EtOAc/hexanes to give the title compound 13, mp 174–175.5° C.;

MS (ESI+) for C$_{17}$H$_{14}$N$_2$O$_3$F$_2$ m/z 333 (M+H)$^+$.

Step 2: Preparation of N-[[(5S)-(−)-3-(3,3-difluoro-2,3-dihydro-1-methyl-2-oxo-1H-indol-5-yl)-2-oxo-5-oxazolidinyl]methyl]acetamide

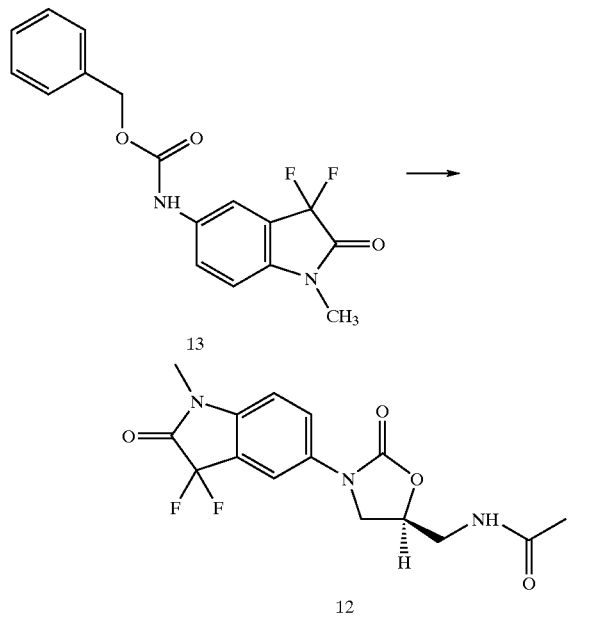

13

12

A mixture of benzyl 3,3-difluoro-1-methyl-2-oxo-2,3-dihydro-1H-indol-5-ylcarbamate 13 (Step 1, 300 mg, 0.903 mmol), (1S)-2-(acetylamino)-1-(chloromethyl)ethyl acetate (350 mg, 1.81 mmol) and MeOH (73 μL, 1.81 mmol) in dry DMF (0.6 mL) under $N_2$ is cooled in an ice bath and treated with LiOtBu (1M in hexanes, 2.71 mL, 2.71 mmol) dropwise over 5 mins. The resulting biphasic mixture is stirred at 0° C. for 30 mins and at ambient temperature for 21 h and is then quenched with glacial acetic acid (104 μL, 2 equiv.), diluted with MeOH (5 mL) and the layers are separated. The MeOH/DMF layer is then diluted with $H_2O$ (15 mL) and extracted with EtOAc (3×25 mL), and the combined EtOAc layer is washed with $H_2O$ (2×20 mL) and saline (20 mL), dried over anhydrous magnesium sulfate and concentrated under reduced pressure. The residue is chromatographed on a Flash 40S 40 g silica gel cartridge, eluting with a gradient of MeOH/$CH_2Cl_2$ (2/98–4/96), and those fractions with an $R_f$=0.20 by TLC (MeOH/$CHCl_3$, 5/95) are pooled and concentrated to give the title compound 12, mp 125–127° C.; MS (ESI+) for $C_{15}H_{15}N_3O_4F_2$ m/z 340 (M+H)$^+$.

Example 6

N-[[(5S)-(−)-3-(3,3-Difluoro-2,3-dihydro-1-ethyl-2-oxo-1H-indol-5-yl)-2-oxo-5-oxazolidinyl]methyl]acetamide

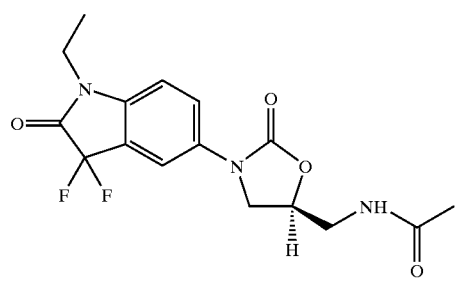

14

Step 1: Preparation of benzyl 3,3-difluoro-1-ethyl-2-oxo-2,3-dihydro-1H-indol-5-ylcarbamate

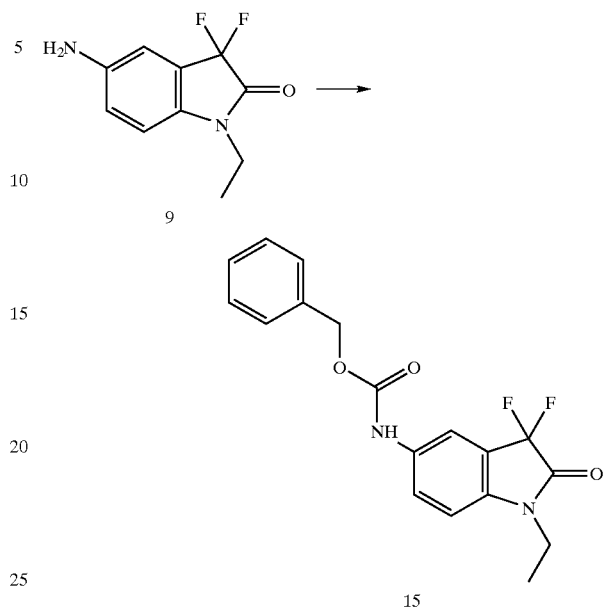

9

15

Following the general procedure of EXAMPLE 5, Step 1, and making non-critical variations but substituting 5-amino-3,3-difluoro-1-ethyl-1,3-dihydro-2H-indol-2-one 9 (EXAMPLE 3, Step 2) for 5-amino-3,3-difluoro-1-methyl-1,3-dihydro-2H-indol-2-one 4, the title compound 15 is obtained, mp 152–154° C.; MS (ESI−) for $C_{18}H_{16}N_2O_3F_2$ m/z 345 (M−H)$^−$.

Step 2: Preparation of N-[[(5S)-(−)-3-(3,3-difluoro-2,3-dihydro-1-ethyl-2-oxo-1H-indol-5-yl)-2-oxo-5-oxazolidinyl]methyl]acetamide

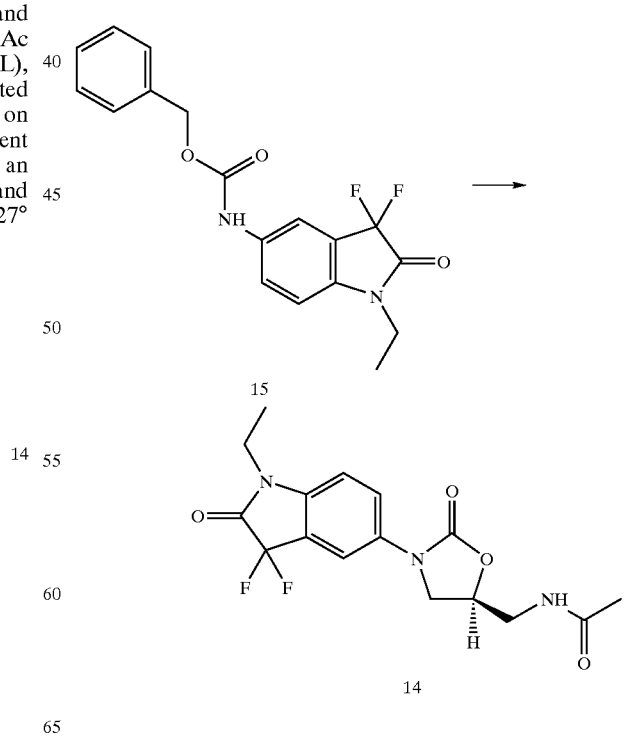

15

14

Following the general procedure of EXAMPLE 5, Step 2, and making non-critical variations but substituting benzyl 3,3-difluoro-1-ethyl-2-oxo-2,3-dihydro-1H-indol-5-ylcarbamate 15 (Step 1) for benzyl 3,3-difluoro-1-methyl-2-oxo-2,3-dihydro-1H-indol-5-ylcarbamate 13 and recrystallizing the product from $CH_2Cl_2/Et_2O$ following chromatography, the title compound 14 is obtained, mp 139–141° C.; MS (ESI+) for $C_{16}H_{17}N_3O_4F_2$ m/z 354 (M+H)$^+$; $[\square]^{25}_D$ –22 (c 0.98, DMSO).

Antibacterial Activity:

MIC Test Method

The in vitro MICs of test compounds were determined by a standard agar dilution method. A stock drug solution of each analog was prepared in the preferred solvent, usually DMSO:$H_2O$ (1:3). Serial 2-fold dilutions of each sample are made using 1.0 ml aliquots of sterile distilled water. To each 1.0 ml aliquot of drug was added 9 ml of molten Mueller Hinton agar medium. The drug-supplemented agar was mixed, poured into 15×100 mm petri dishes, and allowed to solidify and dry prior to inoculation.

Vials of each of the test organisms are maintained frozen in the vapor phase of a liquid nitrogen freezer. Test cultures are grown overnight at 35° C. on the medium appropriate for the organism. Colonies are harvested with a sterile swab, and cell suspensions are prepared in Trypticase Soy broth (TSB) to equal the turbidity of a 0.5 McFarland standard. A 1:20 dilution of each suspension was made in TSB. The plates containing the drug supplemented agar are inoculated with a 0.001 ml drop of the cell suspension using a Steers replicator, yielding approximately $10^4$ to $10^5$ cells per spot. The plates are incubated overnight at 35° C.

Following incubation the Minimum Inhibitory Concentration (MIC µg/ml), the lowest concentration of drug that inhibits visible growth of the organism, was read and recorded. The data is shown in Table I.

TABLE I

| Example No. | Compound No. | SAUR 9213[a] MIC | SPNE 9912[c] MIC |
|---|---|---|---|
| 1 | 1 | 2 | 2 |
| 2 | 6 | 2 | 1–2 |
| 3 | 7 | 8 | 4 |
| 4 | 11 | 8 | 4 |
| 5 | 12 | 2 | 1 |
| 6 | 14 | 8 | 2 |

[a]S. aureus
[b]S. pneumoniae

I claim:

1. A compound of Formula I

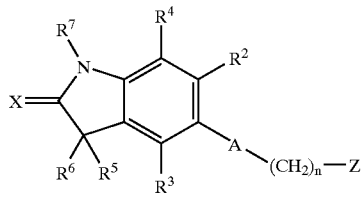

Formula I or a pharmaceutically acceptable salt thereof wherein:

A is structure i;

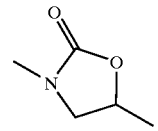

i n is 0 or 1;

X is O, S, NH, Nalkyl, NOH, and NOalkyl;

Z is NHC(=O)R$^1$, NHC(=S)R$^1$, C(=O)NHR$^1$, C(=O)N(H)OH, or NHC(=NCN)R$^1$;

R$^1$ is H, NH$_2$, NHC$_{1-4}$alkyl, C$_{1-4}$alkyl, C$_{2-4}$alkenyl, —(CH$_2$)$_m$C(=O)C$_{1-4}$alkyl, OC$_{1-4}$alkyl, SC$_{1-4}$alkyl, (CH$_2$)$_m$C$_{3-6}$cycloalkyl, the alkyl optionally being a substituted alkyl;

R$^2$ and R$^3$ are independently H or F;

R$^4$ is H, Cl, F, CH$_3$, CF$_3$, NH$_2$, NO$_2$ or CN;

R$_5$ and R$_6$ are independently H, alkyl, substituted alkyl, -Salkyl, -Oalkyl, alkenyl, substituted alkenyl, hydroxy, aryl or halo;

R$_7$ is H, alkyl, substituted alkyl, cycloalkyl, C(=O)alkyl, C(=O)substituted alkyl, aryl, alkenyl, or substituted alkenyl; and each m is independently 0, 1 or 2.

2. The compound of claim 1, wherein R$_7$ is alkyl or substituted alkyl.

3. The compound of claim 1, wherein R$_5$ is halo.

4. The compound of claim 1, wherein R$_6$ is halo.

5. The compound of claim 1, which is:
   a) (5R)-(–)-3-(3,3-difluoro-2,3-dihydro-1-methyl-2-oxo-1H-indol-5-yl)-N-methyl-2-oxo-5-oxazolidinecarboxamide;
   b) (5R)-(–)-3-(3,3-difluoro-2,3-dihydro-1-methyl-2-oxo-1H-indol-5-yl)-2-oxo-5-oxazolidinecarboxamide;
   c) (5R)-(–)-3-(3,3-difluoro-2,3-dihydro-1-ethyl-2-oxo-1H-indol-5-yl)-2-oxo-5-oxazolidinecarboxamide;
   d) (5R)-(–)-3-(3,3-difluoro-2,3-dihydro-1-ethyl-2-oxo-1H-indol-5-yl)-N-methyl-2-oxo-5-oxazolidinecarboxamide;
   e) N-[[(5S)-(–)-3-(3,3-difluoro-2,3-dihydro-1-methyl-2-oxo-1H-indol-5-yl)-2-oxo-5-oxazolidinyl]methyl] acetamide; or
   f) N-[[(5S)-(–)-3-(3,3-difluoro-2,3-dihydro-1-ethyl-2-oxo-1H-indol-5-yl)-2-oxo-5-oxazolidinyl]methyl] acetamide.

6. A method for the treatment of microbial infections in mammals comprising administration of an effective amount of compound of claim 1 to said mammals.

7. The method of claim 6 wherein said compound is administered to the mammal orally, parenterally, transdermally, or topically.

8. The method of claim 6 wherein said compound is administered in an amount of from about 0.1 to about 1000 mg of the compound of claim 1.

9. The method of claim 6 wherein said compound is administered in an amount of from about 0.1 to about 500 mg of the compound of claim 1.

10. A pharmaceutical composition comprising a compound of claim 1 and a pharmaceutically acceptable carrier.

* * * * *